(12) United States Patent
O'Hara et al.

(10) Patent No.: US 7,330,270 B2
(45) Date of Patent: Feb. 12, 2008

(54) METHOD TO SUPPRESS ARTIFACTS IN FREQUENCY-DOMAIN OPTICAL COHERENCE TOMOGRAPHY

(75) Inventors: Keith E. O'Hara, Pleasanton, CA (US); Martin Hacker, Pleasanton, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 214 days.

(21) Appl. No.: 11/334,964

(22) Filed: Jan. 19, 2006

(65) Prior Publication Data

US 2006/0171503 A1   Aug. 3, 2006

Related U.S. Application Data

(60) Provisional application No. 60/714,721, filed on Sep. 7, 2005, provisional application No. 60/645,791, filed on Jan. 21, 2005.

(51) Int. Cl.
*G01N 21/90*   (2006.01)
*G01J 3/45*   (2006.01)

(52) U.S. Cl. .................. 356/479; 356/456; 356/497

(58) Field of Classification Search .............. 356/479, 356/489, 497, 456
See application file for complete search history.

(56) References Cited

U.S. PATENT DOCUMENTS

| | | | |
|---|---|---|---|
| 5,321,501 A * | 6/1994 | Swanson et al. | 356/479 |
| 5,956,355 A | 9/1999 | Swanson et al. | 372/20 |
| 6,282,011 B1 * | 8/2001 | Tearney et al. | 359/287 |
| 6,385,358 B1 * | 5/2002 | Everett et al. | 385/12 |
| 6,615,072 B1 | 9/2003 | Izatt et al. | 600/478 |
| 6,618,152 B2 | 9/2003 | Toida | 356/479 |
| 6,882,431 B2 | 4/2005 | Teich et al. | 356/497 |
| 7,102,756 B2 * | 9/2006 | Izatt et al. | 356/479 |
| 7,256,894 B2 * | 8/2007 | Chen et al. | 356/497 |
| 2003/0137669 A1 * | 7/2003 | Rollins et al. | 356/479 |
| 2004/0239938 A1 * | 12/2004 | Izatt | 356/450 |
| 2005/0171438 A1 * | 8/2005 | Chen et al. | 600/476 |
| 2006/0192969 A1 * | 8/2006 | Marks et al. | 356/451 |

OTHER PUBLICATIONS

Francois, Monerie, Vassallo, Durteste, and Alard; Three Ways to Implement Interferencial Techniques: Application to Measurements of Chromatic Dispersion, Birefringence, and Nonlinear Susceptibilities; Mar. 1989; Journal of Lightwave Technology, vol. 7, No. 3, pp. 500-513.*

In re U.S. Appl. No. 10/933,795, filed Sep. 3, 2004, by Matthew Everett et al., entitled A patterned spinning disk based optical phase shifter for spectral domain optical coherence tomography.

(Continued)

*Primary Examiner*—Layla G. Lauchman
*Assistant Examiner*—Scott M Richey
(74) *Attorney, Agent, or Firm*—Stallman & Pollock LLP

(57) ABSTRACT

One embodiment of the present invention is a method for suppressing artifacts in frequency-domain OCT images, which method includes (a) providing sample and reference paths with a significant difference in their chromatic dispersion (b) correcting for the effects of the mismatch in chromatic dispersion, for the purpose of making artifacts in the OCT image readily distinguishable from the desired image.

21 Claims, 7 Drawing Sheets

OTHER PUBLICATIONS

M.A. Choma, et al., "Sensitivity advantage of swept source and Fourier domain optical coherence tomography," *Optics Express*, vol. 11, No. 18, Sep. 8, 2003, pp. 2183-2189.

M. Cyganek et al., "Numerical estimation of the total phase shift in Complex Spectral OCT in vivo imaging," *Coherence Domain Optical Methods and Optical Coherence Tomography in Biomedicine VIII, Proceedings of SPIE*, vol. 5316, (2004), pp. 248-251.

J. F. de Boer et al., "Improved signal-to-noise ratio in spectral-domain compared with time-domain optical coherence tomography," *Optics Letters*, vol. 28, No. 21, Nov. 1, 2003, pp. 2067-2069.

A.F. Fercher et al. "Numerical dispersion compensation for Partial Coherence Interferometry and Optical Coherence Tomography," *Optics Express*, vol. 9, No. 12, Dec. 3, 2001, pp. 610-615.

A.F. Fercher et al., "Dispersion compensation for optical coherence tomography depth-scan signals by a numerical technique," *Optics Communications*, vol. 204, Apr. 1, 2002, pp. 67-74.

C.K. Hitzenberger et al., "Dispersion Effects in Partial Coherence Interferometry: Implications for Intraocular Ranging" *Journal of Biomedical Optics*, vol. 4, No. 1, Jan. 1999, pp. 144-151.

R. Leitgeb et al., "Performance of fourier domain vs. time domain optical coherence tomography," *Optics Express*, vol. 11, No. 8, pp. 889-894, 2003.

R.A. Leitgeb et al., "Phase-shifting algorithm to achieve high-speed long-depth-range probing by frequency-domain optical coherence tomography," *Optics Letters*, vol. 28, No. 22, Nov. 15, 2003, vol. 28, No. 22, pp. 2201-2203.

D.L. Marks et al., "Digital algorithm for dispersion correction in optical coherence tomography for homogeneous and stratified media," *Applied Optics*, vol. 42, No. 2, Jan. 10, 2003, pp. 204-217.

Book by B.E.A. Saleh et al., *Fundamentals of Photonics*, Chapter 5, entitled "Exercise 5.5-1," published by John Wiley and Sons, Copyright 1991, pp. coversheet+1, 176-191.

Book by A.E. Siegman, *Lasers*, Chapter 9, entitled "9.3 Group Velocity Dispersion and Pulse Compression," published by University Science Books, Copyright 1986, 11 pages in length.

J.O. Smith et al., "A Flexible Sampling-Rate Conversion Method," *In Proc. IEEE Int. Conf. Acoustic Speech Signal* Processing, vol. 2 (1984), pp. 19.4.1 through 19.4.4.

L.M. Smith et al., "Absolute displacement measurements using modulation of the spectrum of white light in a Michelson interferometer," *Applied Optics*, vol. 28, No. 15, Aug. 15, 1999, pp. 3339-3342.

P. Targowski et al., "Complex spectral OCT in human eye imaging in vivo," *Optics Communications*, vol. 229, (2004), pp. 79-84.

M. Wojtkowski et al. "Real-time in vivo imaging by high-speed spectral optical coherence tomography," *Optics Letters*, vol. 28, No. 19, Oct. 1, 2003, pp. 1745-1747.

M. Wojtkowski et al., "Ultrahigh-resolution, high-speed, Fourier domain optical coherence tomography and methods for dispersion compensation," *Optics Express*, vol. 12, No. 11, May 31, 2004, pp. 2404-2422.

S.H. Yun et al., "Removing the depth-degeneracy in optical frequency domain imaging with frequency shifting," *Optics Express*, vol. 12, No. 20, Oct. 4, 2004, pp. 4822-4828.

\* cited by examiner a  b

METHOD TO SUPPRESS ARTIFACTS IN FREQUENCY-DOMAIN OPTICAL COHERENCE TOMOGRAPHY

PRIORITY

This application claims the benefit of the filing date under 35 U.S.C. § 119(e) of Provisional U.S. Patent Application Ser. No. 60/645,791, filed on Jan. 21, 2005, and to Provisional U.S. Patent Application Ser. No. 60/714,721, filed on Sep. 7, 2005, which are hereby incorporated by reference in their entirety.

TECHNICAL FIELD OF THE INVENTION

One or more embodiments of the present invention relate generally to optical imaging, in particular, methods of frequency-domain optical coherence tomography (OCT) in which the interference signal is measured as a function of optical frequency. The invention is a novel method for suppressing artifacts in OCT images, and in blurring the mirror image present in images acquired by frequency-domain OCT so that it can be clearly distinguished from the real image.

BACKGROUND OF THE INVENTION

Optical Coherence Tomography (OCT) is a technology for performing high-resolution cross sectional imaging that can provide images of tissue structure on the micron scale in situ and in real time. OCT is a method of interferometry that uses light containing a range of optical frequencies to determine the scattering profile of a sample. The axial resolution of OCT is inversely proportional to the span of optical frequencies used.

In recent years, it has been demonstrated that frequency domain OCT has significant advantages in speed and signal to noise ratio as compared to time domain OCT (Leitgeb, R. A., et al., *Optics Express* 11:889-894; de Boer, J. F. et al., *Optics Letters* 28: 2067-2069; Choma, M. A., and M. V. Sarunic, *Optics Express* 11: 2183-2189).

In frequency domain OCT, a light source capable of emitting a range of optical frequencies excites an interferometer, the interferometer combines the light returned from a sample with the light returned from a reference reflector, and the intensity of the combined light is recorded as a function of optical frequency to form an interference spectrum. A Fourier transform of the interference spectrum provides the reflectance distribution along the depth within the sample. Frequency domain OCT requires some means to record the interference spectrum, the intensity of light output from the interferometer as a function of optical frequency. Current methods of Frequency domain OCT can be divided into two categories.

In spectral-domain OCT, a grating or prism or other means is used to disperse the output of the interferometer into its optical frequency components. The intensities of these separated components are measured using an array of optical detectors, each detector receiving an optical frequency or a fractional range of optical frequencies. The set of measurements from these optical detectors forms an interference spectrum (Smith, L. M. and C. C. Dobson, *Applied Optics* 28: 3339-3342). Typically the light source emits a broad range of optical frequencies simultaneously.

Alternatively, in swept-source OCT, the interference spectrum is recorded by using a source with adjustable optical frequency, with the optical frequency of the source swept through a range of optical frequencies, and recording the interfered light intensity as a function of time during the sweep (Swanson, E, et al., U.S. Pat. No. 5,321,501).

Frequency-domain OCT efficiently uses the light returned from a range of depths within the sample, as all the returned light contributes to the modulation in the interference spectrum. This is in contrast to the case of time domain OCT, in which the interference signal is sensitive only to light returned from depths in the sample that match the current length of the reference arm to within the coherence length of the source. For a given illumination level and time of exposure, the achievable signal to noise ratio is substantially greater in frequency-domain OCT than in time-domain OCT (Leitgeb, R. A. et al., *Optics Express* 11: 889-894; de Boer, J. F. et al., *Optics Letters* 28: 2067-2069; Choma, M. A., and M. V. Sarunic, *Optics Express* 11: 2183-2189).

Chromatic dispersion is a property of an optical element that characterizes the degree by which the optical path length through that element varies across a range of optical frequencies. OCT determines the position in the sample of a scattering center based on the difference in optical group delay between two optical paths: 1) the path of light scattered from the sample, and 2) a reference optical path. Most OCT literature refers simply to the difference between sample and reference optical path lengths; but when one considers chromatic dispersion one must distinguish between the phase delay and the group delay associated with a given optical path length. OCT is sensitive to the difference in group delay (see, for example, section 2.1 in Fercher et al., *Optics Express* 9: 610-615). OCT necessarily uses a range of optical frequencies. If the chromatic dispersion is not matched between the two paths, the apparent position of the scattering center depends on the optical frequency used. A mismatch in chromatic dispersion thus broadens the axial resolution of the OCT as explained by Hitzenberger et al., (*Journal of Biomedical Optics* 4: 144-151). For this reason, in most OCT systems the chromatic dispersion is closely matched between sample and reference paths (see, for example, U.S. Pat. Nos. 6,385,358, 6,615,072, 6,618,152) sometimes through the use of dispersive optical devices (see, for example U.S. Pat. No. 6,282,011). One of the advantages of quantum OCT (a method of time-domain OCT described by Teich et al. in U.S. Pat. No. 6,882,431) is that it partially cancels the mismatch in chromatic dispersion between the sample and reference paths.

Since a perfect match of chromatic dispersion is not simple and can add cost to a frequency domain OCT system, numerical correction of the residual mismatch in chromatic dispersion has been described by Fercher et al. (*Optics Express* 9: 610-615; *Optics Communications* 204: 67-74) and by Marks et al. (*Applied Optics* 42: 204-217). The preceding authors used a test sample to determine the residual mismatch in chromatic dispersion. Alternatively, the numerical correction for dispersion can be empirically adjusted for best sharpness of the resulting OCT image, without using a test sample, as described by Wojtkowski et al. (*Optics Express* 12: 2404-2422).

Frequency domain methods of OCT use the fact that interference between light scattered from the sample and the reference beam causes spectral interference fringes, a modulation in the intensity of the combined beam as a function of optical frequency. The spacing of the interference fringes depends on the difference in optical group delay between the light scattered from the sample, and reference light. In addition to chromatic dispersion match or correction, there are two additional major issues associated with this method.

The first one is that the spacing of the interference fringes does not depend on which of the two paths is longer. Therefore, simple methods of frequency-domain OCT do not distinguish between scattering from a sample location corresponding to an optical group delay a certain amount longer than that of the reference path, and scattering with an optical group delay the same amount shorter than that of the reference path. The resulting image contains the true scattering profile plus the superposed mirror image of the scattering profile. (See, for example, Yun et al., *Optics Express* 12:4822-4828.)

Phase shifting one of the interfering beams has been proposed to remove the mirror image in spectral domain OCT, but to date these methods leave some residual image and are complicated and costly (Leitgeb, R. A. et al., *Optics Letters* 28: 2201-2203; Izatt et al. U.S. Patent Publication No. 2004/0239938; co-pending U.S. patent application Ser. No. 10/933,795; Sarunic, et al., SPIE 5316: 241-247). In particular, sequential phase shift does not produce a good result if the sample such as a human eye tends to move during the period when the multiple phase interference spectrums are recorded (Targowski et al., *Optics Communications,* 229:79-84). On the other hand, simultaneous parallel multi-phase detection of the interference spectrum would require the use of at least two spectrometers or two detector arrays in the spectrometer, which will not only add complication in terms of optical alignment but also substantially increase the spectrometer cost. Frequency shifting one of the interfering beams in swept-source OCT has been used to shift the image away from its mirror image (Yun et al., *Optics Express* 12: 4822-4828), but this method is applicable only in situations where the sample being imaged has finite visible extent, and in which the detection electronics can accept the resulting higher-frequency signal. In addition, it requires an additional optical frequency shifter which is an expensive item and hence would add cost to the OCT system.

The second issue is that when the interference spectrum is recorded as a function of optical frequency, periodic interfering signals as a function of optical frequency can corrupt the digitized spectrum. For example, in the case of spectral-domain OCT, the readout electronics of the array detector often adds periodic pattern noise to the recorded optical intensities. In swept-source OCT, electronic clocks and counters can add a similar periodic error signal. Furthermore, a spectral ripple of the light source, such as those caused by etalon effects from inadvertent reflections in path from the light source, causes a periodic error signal in the recorded interference spectrum.

The periodic error signal from these and similar sources is difficult to distinguish from the interference fringes caused by light scattered from the sample. If present in the spectra when the image is reconstructed, the periodic error signal will cause the artificial appearance of a scattering center at a particular depth in the reconstructed image. The periodic error signal can be partially removed by measuring it separately from the measurement on the sample, and subtracting them from measurements on the sample. Such correction methods work only to the extent that the periodic error signal repeats exactly, in both amplitude and phase, on each spectrum acquisition. Signals from non-synchronized clocks, for example, will not repeat exactly and cannot be cancelled in this way.

From the above discussions, it can be seen that previous frequency-domain OCT systems generally require a match in the chromatic dispersion characteristics of the two interferometer paths and even with a perfect match or a correction of the residual mismatch, the existing methods cannot cost-effectively address the issue of a mirror image and the artifacts induced by periodic spectral noise from either the source or the detector, there is hence a need in the art of frequency domain OCT to remove the stringent requirement of chromatic dispersion match, to easily and clearly distinguish the mirror image from the real image and to substantially suppress the image artifacts due to periodic spectral error signals.

SUMMARY OF THE INVENTION

One or more embodiments of the present invention satisfy one or more of the above-identified needs in the art. In particular, one embodiment of the present invention is a method for optical coherence tomography wherein the chromatic dispersion differs significantly between sample path and reference path, and the measured interference spectrum is multiplied by a complex phase factor to compensate for the chromatic dispersion.

One aspect of the present invention is to use the blurring effects of chromatic dispersion on OCT images to allow the viewer to distinguish the real image from the mirror image artifact in the resulting OCT tomogram, these blurring effects being corrected by multiplication by the complex phase factor only for the true, non-mirrored image.

Another aspect of the present invention is to use the blurring effects of chromatic dispersion on OCT images to substantially suppress the artifacts in the real image due to periodic interfering signals in the frequency-domain OCT measurement Another aspect of the present invention is the use of different materials in the sample and reference arms of the OCT system to achieve a difference in chromatic dispersion between these arms.

Another aspect of the present invention is to use the blurring effects of chromatic dispersion on undesired artifacts in OCT images, so as to provide a measure of the degree of rejection of these artifacts.

These and other features and advantages of the present invention will become more readily apparent to those skilled in the art upon review of the following detailed description of the preferred embodiments taken in conjunction with the accompanying drawings.

DETAILED DESCRIPTION

Implementations of swept-source OCT are described by Swanson and Chinn (U.S. Pat. No. 5,956,355) and a modern implementation of spectral-domain OCT is described by Wojtkowski, et al. (*Optics Express* 12: 2404-2422). The common features of these two frequency-domain OCT techniques are reviewed here.

Figure 1:
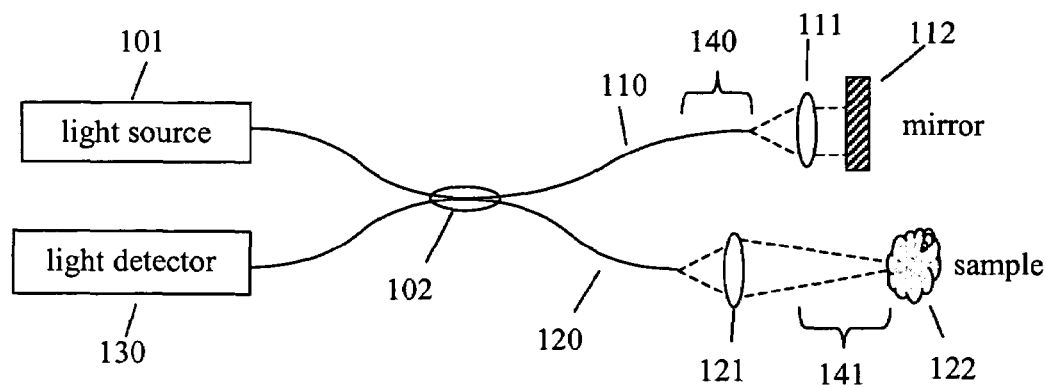
FIG. 1 is a schematic illustration of an OCT interferometer.

FIG. 1 illustrates an example of an OCT interferometer. Light from source 101 is directed to beamsplitter 102, illustrated here as a fiber beamsplitter, that separates light from the source between the reference fiber 110 and sample fiber 120. Some light directed toward sample 122 by lens 121 is scattered by the sample and returned through sample path 120. Some light collimated by lens 111 and reflected from the reference mirror 112 is returned through reference fiber 110. Light returned from the mirror is combined with light returned from the sample in beamsplitter 102 to form an interference signal, and some of the combined light is directed to the detector 130.

In frequency-domain OCT, the interference is recorded as a function of optical frequency. In spectral-domain OCT, detector 130 separates the combined light into its optical frequency components, using a spectrometer and a camera or other means, and provides as output the interference spectrum as a function of optical frequency. In swept-source OCT, source 101 is swept through a range of optical frequencies, and the output of detector 130 at each time during a sweep is associated with the optical frequency concurrently output from source 101.

Referring to FIG. 1, significant mismatch in optical dispersion can be introduced by the choice of lengths of optical paths in fiber and air. Consider the case when fiber 110 is 100 mm longer than fiber 120, but the lenses 111 and 121 are of substantially the same thickness. The extra length of fiber 110 is indicated by label 140. Consider for simplicity the situation when the region of interest in the sample is close to the surface, so that there is negligible chromatic dispersion within the sample. The extra optical path length due to the longer fiber 110 can be balanced at a particular optical frequency by placing approximately 150 mm more optical path in air in the sample path than in the reference path, indicated by label 141. The exact path length in air can be adjusted so that the sample and reference optical path lengths match for the optical frequency at the center of the spectrum of the source.

For wavelengths near 800 nm, the optical path length in glass fiber varies with optical wavelength by approximately 0.12 fs/nm per mm of fiber (Saleh, B. E. A, and M. C. Teich *Fundamentals of Photonics*, chapter 5). Multiplication by the speed of light gives this dispersion in terms of optical path length in vacuum: 0.036 µm/nm per mm of fiber. Therefore the 100 mm extra fiber causes the optical path length difference, between sample and reference arms, to vary across the spectrum by 3.6 µm/nm. Considering that light passes the extra fiber twice between leaving the source and reaching the detector, the complete optical path length difference, between the complete sample and reference paths, varies by 7.2 µm/nm. A broadband source with full-with at half-maximum intensity equal to 30 nm gives 10-micron axial resolution in OCT (using equation (1) in Fercher, et al., *Optics Communications* 204: 67-74). The mismatched dispersion we consider in this example causes the apparent location of a scattering center to vary by 100 µm across the 30 nm bandwidth of the source.

Referring again to FIG. 1, an alternative method of introducing mismatched chromatic dispersion is to use a mirror with significant chromatic dispersion in the position of mirror 112. For example, Siegman (*Lasers*, section 9.3) describes use of a Gires-Tournois interferometer, or a sequence of prisms, or a pair of diffraction gratings, for this purpose of introducing chromatic dispersion.

Figure 2:
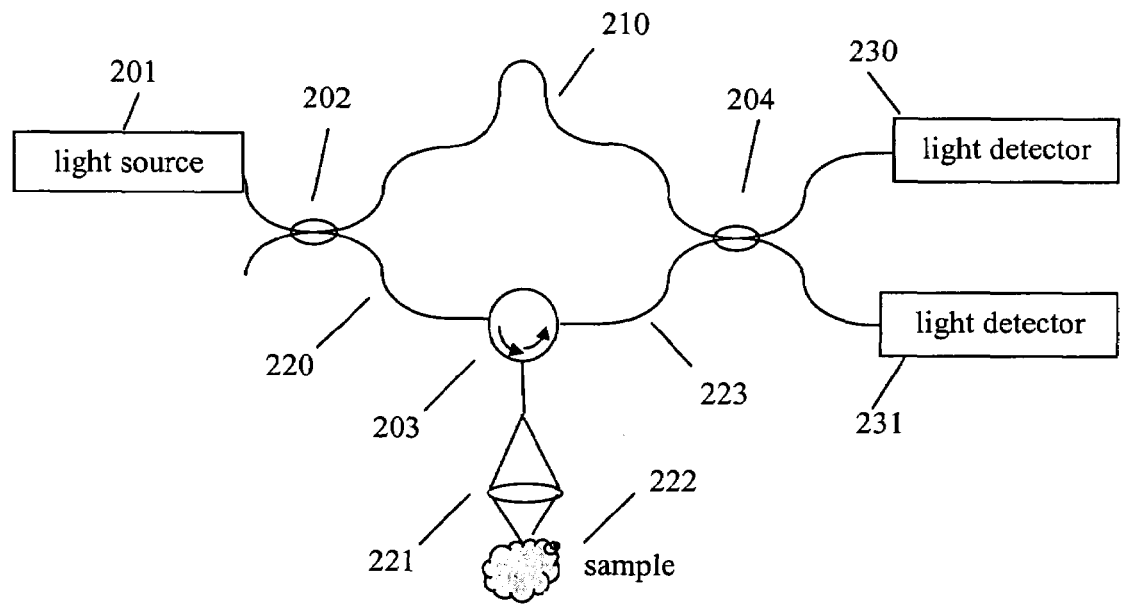
FIG. 2 is a schematic illustration of an alternative OCT interferometer.

Alternative to the Michelson interferometer architecture shown in FIG. 1, other interferometer architectures can be used for frequency-domain OCT, such as the Mach-Zehnder configuration shown in FIG. 2. Light from source 201 is directed to beamsplitter 202 that separates light between the reference fiber 210 and sample fiber 220. Circulator 203 directs light from sample fiber 220 toward lens 221. Some light directed toward sample 222 by lens 221 is scattered by the sample and returned to circulator 203. Circulator 203 directs the light returned by the sample to fiber 223. Beamsplitter 204 combines sample light from fiber 223 with reference light from fiber 210, and the outputs of beamsplitter 204 are directed to detectors 230 and 231. In FIG. 2, the circular can be replaced by a fiber beamsplitter that directs some of the light from fiber 220 to the sample 222, and directs some of the light returned from sample 222 to fiber 223.

In FIG. 2 there are several opportunities for creating a significant mismatch in chromatic dispersion. The reference path as drawn contains no optical path in air, so the portion of the sample path that is in air is balanced by additional length of reference fiber 210. Use of different materials in sample and reference paths causes the relative optical lengths of these paths to vary with optical frequency, as seen above in relation to FIG. 1. Alternatively, the optical circulator can also be designed to give significant dispersion. As another alternative, the fiber 210 can be broken and the optical path reflected off a mirror with chromatic dispersion, such as a chirped dielectric mirror or a Gires-Tournois interferometer.

Let the light incident on the sample have electric field amplitude $E_0$. Then the light scattered from the sample and accepted back into the interferometer has electric field $$E_S = E_0 \int r(z) e^{2iqz} dz \times \exp\left[i \int_S 2\pi n_S / dz\right]$$

where r(z) is the amplitude-reflection coefficient of the sample at depth z, $q=2\pi n/\lambda$ is the spatial optical frequency of the light in the sample, the variable $\lambda$ denotes the wavelength of the light in vacuum, n is the average refractive index within the region of interest in the sample, and $n_S$ is a function along the path S with values equal to the refractive indices of the various materials along the sample path.

The equation in the preceding paragraph divides the phase accumulated by the light wave into two parts. The integral containing r(z) accounts for the phase accumulated from the end of path S to the individual scattering centers in the sample. The integral over the path S accounts for the phase accumulated within the instrument. The path S is along the optical path from the source to the reference depth z=0 in the sample, and then from the depth z=0 in the sample following the optical path to one of the detectors. The refractive index $n_S$ is a function of position determined by the materials along the optical path S.

In general the refractive index in the sample n depends on both position z and on λ, but in the preferred embodiment we define q=2πn/λ using a spatially averaged refractive index n that depends on wavelength λ only. Inclusion of the wavelength-dependent but spatially averaged refractive index in the definition of q compensates for the spatially averaged chromatic dispersion of the material in the sample. Marks et al. (*Applied Optics* 42: 204-217, section 3) describe reconstruction methods to correct for non-uniform chromatic dispersion within the sample, which methods can optionally be used in conjunction with the present invention.

Similarly, the light returned from the reference path has electric field $$E_R = \alpha E_0 \times \exp\left[i \int_R 2\pi n_R / \lambda \, dz\right]$$

where α is a real number relating the amplitude of the light returned by the reference path to that incident on the sample, the path of integration R is along the optical path of the reference light from source to the detector, and the refractive index $n_R$ is a function of position determined by the materials along the optical path R.

The two integrals over paths R and S add a net optical phase, denoted by $\phi_D$, in addition to the phase determined by the structure of the sample through r(z):

$$\phi_D = \int_S 2\pi n_S / \lambda \, dz - \int_R 2\pi n_R / \lambda \, dz.$$

The phase mismatch $\phi_D$ is a function of optical frequency q. For ease of understanding the method, it is convenient to take the paths R and S to have the same group delay, meaning that $d\phi_D/dq=0$ at the center of the spectrum used for OCT. The important quality of $\phi_D$ is its higher-order derivatives in q.

The optical power from one port of the interferometer, at optical frequency q, is $$P(q) = |E_R + E_S|^2 + \text{noise}$$

$$= |E_R|^2 + 2\alpha|E_0|^2 \int r(z)\cos(2qz + \phi_D) dz + |E_S|^2 + \text{noise}$$

$$= |E_R|^2 + \alpha|E_0|^2 \int r(z)e^{i2qz+i\phi_D} dz +$$

$$\alpha|E_0|^2 \int r(z)e^{-i2qz-i\phi_D} dz + |E_S|^2 + \text{noise}$$

where $|E_R|^2$ is the power entering the spectrometer from the reference arm, and $|E_S|^2$ is returned from the sample, out of $|E_0|^2$ power incident on the sample. The final term noise represents measurement noise and interfering signals. Interfering signals from system clocks, for example, can be introduced into the record of P(q) before digitization, causing artifacts that are easily visible after Fourier transform. The power P(q) is measured by the light detector as a function of optical frequency, and digitized for processing.

The first term, the reference arm power, has the same spectral shape as the source, so it can be cancelled by subtracting a spectrum measured with the sample arm blocked. The last term is the power returned from the sample, and is negligibly small compared with the other terms, given appropriate choice of reference arm power $|E_R|^2$. In cases where $|E_S|^2$ is not small, it is suppressed by the numerical compensation of dispersion, described below, in the same way as the term denoted by noise. The two middle terms are the interference terms; it is difficult to isolate only one of these terms without making a separate measurement with a different phase shift $\phi_D$ between sample and reference arm. In frequency-domain OCT systems that do not use phase shifting, the two interference terms produce two separate images of the sample. The alternate configuration shown in FIG. 2 produces two interference spectra of the form shown above, in which the two outputs have $\phi_D$ differing by 180° as described by US2004/0239938. However, this would require the use of two spectrometers and hence increase the cost of the system.

Figure 3:
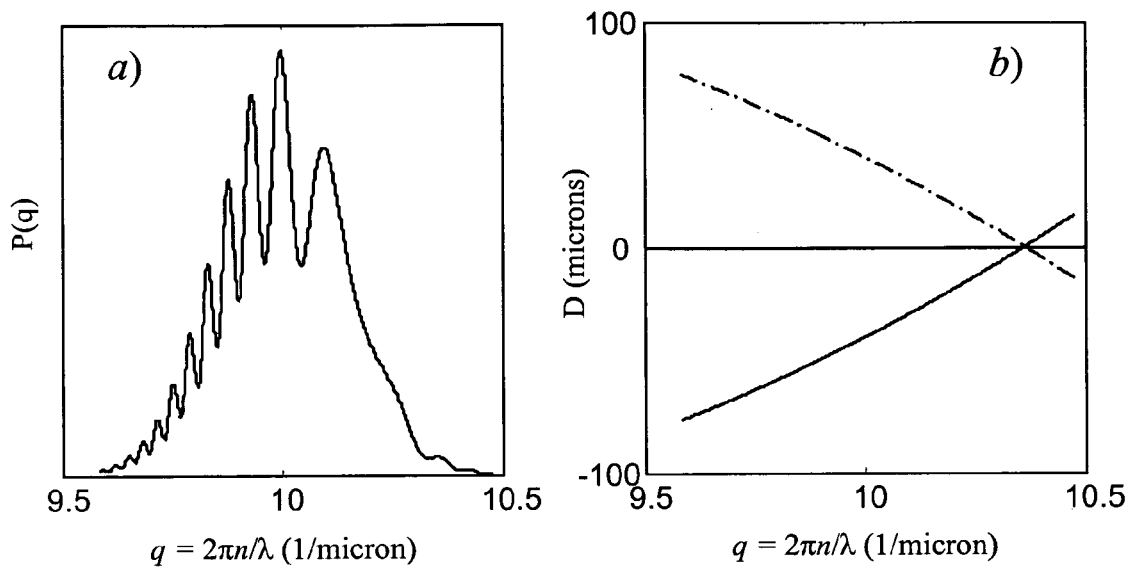
FIG. 3 shows as a function of optical frequency a schematic interference spectrum due to a single scattering center, and the variation in apparent position of the scattering center.

FIG. 3 illustrates how the phase mismatch $\phi_D$ affects the apparent position of a scattering center in the sample. The phase of the fringes in the expression for P(q) above is $\phi=2qz+\phi_D$. The frequency of the interference fringes in the spectrum is related to the derivative of this phase with respect to optical frequency, $(d\phi/dq)/2$. In a system with matched chromatic dispersion, $\phi_D$ can be ignored, so the position of the scattering center is given by $z=(d\phi/dq)/2$. The presence of chromatic dispersion causes the frequency of the interference fringes to vary across the spectrum, and the apparent depth of the scattering center also varies, as $$D \equiv \frac{1}{2}\frac{d\phi}{dq} = z + \frac{1}{2}\frac{d\phi_D}{dq}.$$

The derivative of phase with respect to frequency is generally called group delay. Herein we use the term group delay to denote the derivative of the phase φ with respect to spatial optical frequency q. Thus, the equation above says that the apparent depth varies across the spectrum by one-half the variation in group delay.

FIG. 3a illustrates the spectrum P(q) that would be measured at one output of an interferometer with a single scattering center in the sample path and an intentionally introduced dispersion mismatch of $\phi_D=100$ μm²q²+20 μm³q³. The range of optical frequencies q shown in FIG. 3 corresponds to a source centered at 840 nm and a refractive index n=1.33, appropriate for water and representative of typical biological samples. This dispersion, could be expected in an Michelson interferometer in which the optical delay of 50 mm extra glass in the sample path is balanced by 75 mm extra air in the reference path. The solid curve in FIG. 3b illustrates the apparent depth D of the scattering center. Such an interferometer has more dispersive material in the sample path, so the sample path is relatively longer in the high-optical-frequency (blue) end of the spectrum.

The phase appears in the expression for P(q) above only in the argument of the cosine function. The cosine function is not sensitive to the sign of its argument, so the spectrum P(q) could equally well have come from a scattering center at depth $D=-(d\phi/dq)/2$. The dashed curve in FIG. 3b illustrates the apparent depth D of the scattering center under this alternate interpretation of the spectrum P(q).

After the interference terms are isolated, they are multiplied by a factor $e^{-i\phi_D}$ that corrects the phase of the interference fringes at each measured optical frequency. The correcting phase $\phi_D$ can be an arbitrary function of optical frequency q, and can be determined either from measurement using a test sample, through the method described by Wojtkowski et al. (*Optics Express* 12: 2404-2422) or by other means of determining the mismatch in chromatic dispersion. The corrected interference spectrum has the form:

$$\int r(z)e^{i2qz}dz + \int r(z)e^{-i2qz-i2\phi_D}dz + \text{noise} \times e^{-i\phi_D} = \int r(z)e^{i2qz}dz + \int r(-z)e^{i2qz-i2\phi_D}dz + \text{noise} \times e^{-i\phi_D}.$$

Other numerical methods for correcting the effects of dispersion mismatch have been described elsewhere. The method presented by Wojtkowski et al. (*Optics Express* 12: 2404-2422) includes the additional step of a Hilbert transform before multiplication by a correcting phase factor. The method presented by Fercher et al. (*Optics Communications* 204: 67-74) performs a convolution on the spatial-domain signal r(z) instead of the equivalent multiplication on the spectrum P(q).

Numerical Fourier transform of the corrected interference spectrum yields the desired coefficient of reflection r(z), plus two undesired images from the other terms. The phase $\phi_D$ due to mismatched dispersion varies across optical frequencies q, which causes these undesired images to be blurred. The term noise has a contribution from readout electronics of the detector or detectors, and this contribution often has a periodic structure, which produces sharp peaks at constant z in the image if not dealt with otherwise; the phase factor introduced numerically desirably blurs these sharp peaks, reducing their peak intensity.

Figure 4:
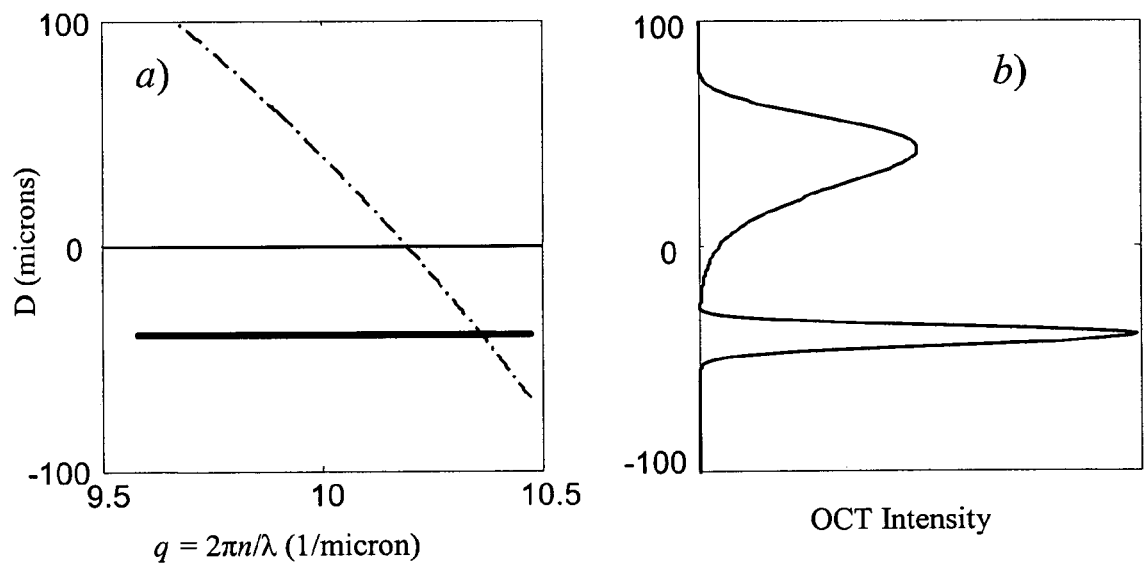
FIG. 4 shows as a function of optical frequency the corrected apparent position of the single scattering center from FIG. 3, and the corresponding reflectance distribution.

FIG. 4a illustrates apparent depth of the scatter considered in FIG. 3a, after correction for dispersion mismatch. The phase of the fringes in the first term of the expression above for the corrected data is $\phi=2qz$, while the phase of the fringes in the second term is $\phi=-2qz-2\phi_D$. An apparent depth can be defined again as $D\equiv(d\phi/dq)/2$ and this depth is plotted in FIG. 4a for each of the two terms in the expression for the corrected data. One of the terms results in a constant apparent depth while the other results in an apparent depth that varies across optical frequencies by twice as much as before correction. This apparent depth is introduced only for illustration; it is not directly computed in the processing of OCT data. Instead, the Fourier transform of the corrected data produces peaks at positions corresponding to these apparent depths. The intensity of the Fourier transform of the corrected spectrum is plotted as an image in FIG. 4b. Intensity is plotted horizontally, and apparent position is plotted on the vertical axis to match FIG. 4a.

The axial resolution of an OCT system is typically defined as the full-width in z at half-maximum of the magnitude of the coefficient of reflection |r(z)| determined by the OCT measurement, with a sharp reflector as the sample. The bandwidth of the source is one limit to the axial resolution; for a Guassian source with full-width at half maximum intensity $\Delta\lambda$ in wavelength, the axial resolution $\delta z$ is $$\delta z \geq \frac{2\ln 2}{\pi}\frac{\lambda^2}{n\Delta\lambda}$$

(Wojtkowski et al., *Optics Express* 12: Page: 2404-2422). The corresponding relation in terms of optical frequency q is $$\delta z \geq \frac{4\ln 2}{\Delta q}.$$

The range of optical frequencies recorded by the detector also limits the axial resolution. Following the convention of Wojtkowski et al. (*Optics Express* 12: Page: 2404-2422) we require that reflections separated by half the axial resolution, $\delta z/2$, produce interference spectra that differ by at least one fringe in the number of fringes produced within the range of optical frequencies recorded. Under this convention the axial resolution is limited by $$\delta z \geq \frac{\lambda^2}{n\Delta\Lambda} = \frac{2\pi}{\Delta Q},$$

where $\Delta\Lambda$ denotes the range of wavelengths recorded and $\Delta Q$ the corresponding range of optical frequencies. We define the axial resolution of an OCT system to be the minimum $\delta z$ supported by both the source width and the range of recorded optical frequencies.

The image artifacts caused by periodic interfering signals are reduced in intensity by the correction of mismatched chromatic dispersion. Consider a particular periodic signal, noise=$A \cos(fq) \times e^{-i\phi_D}$, which would cause a spike of amplitude A in the Fourier transform if there were no correction factor $e^{-i\phi_D}$. We consider again the conditions considered in relation to FIG. 1: 100 mm extra fiber in the reference arm producing a variation in apparent depth of 3.6 µm/nm. The corresponding phase correction is $\phi_D$=370 µm$^2$q$^2$. If the source has 30 nm full-width at half-maximum intensity, then the set of optical frequencies recorded would likely correspond to 50 nm. Evaluating the Fourier transform of noise as defined above, over this range of optical frequencies, yields 0.24 A. The amplitude of the artifact is reduced by a factor of four. If the artifact were interpreted as light reflected from the sample, this reduction corresponds to a factor of sixteen reduction in intensity of reflected light.

Applying the correction factor $e^{-i\phi_D}$ to a periodic noise term spreads the resulting intensity in the Fourier transform to the same degree as the actual chromatic dispersion would have spread the signal from a scattered point in the sample. By Parseval's theorem the integrated energy in the Fourier transform is not affected by the phase correction $e^{-i\phi_D}$. Thus the peak intensity is reduced by the same factor as the width is increased.

Figure 5:
FIG. 5 shows OCT images of human eye tissue, with the undesired mirror images significantly blurred by the technique disclosed here.

FIG. 5 illustrates the asymmetry between the desired and mirror image due to an intentional dispersion mismatch. Each column of this image is the measurement of r(z) at a different transverse location. The pixel intensities are proportional to log(|r(z)|), with darker grey corresponding to stronger scattering. The OCT measurement is repeated at neighboring locations on the sample, with neighboring measurements forming adjacent columns in the raster image. The degree of chromatic dispersion mismatch was enough to cause a phase mismatch variation of $\phi_D$=640 µm$^2\Delta[(2\pi/\lambda)^2]$, where the operator $\Delta$ denotes the change in the quantity in square brackets from its value at the center of the spectrum.

FIG. 5 illustrates a situation in which the desired image 501 overlaps with the mirror image 502. Residual artifacts from imperfectly cancelled background $|E_R|^2$ and low-frequency noise in the spectrum P(q), the autocorrelation term $|E_S|^2$, appears at the location z=0 indicated by label 503. The desired image is easily distinguished from the mirror image, which appears inverted and blurred in this presentation. By evaluating the image in FIG. 5, the operator can easily orient himself to the situation and move the sample down in the field of view, so as to obtain an image well separated from artifacts, such as that shown in FIG. 6b.

The apparent depth D of the scattering centers varies by approximately 450 μm over the spectral range of $\Delta Q \approx 0.7/\mu m$ that was recorded to produce the image in FIG. 5, while the axial resolution of the compensated image is approximately 10 μm. Typically, the true image can be readily distinguished from the mirror image if the variation in D across the recorded spectrum is five or more times the axial resolution. In either the Michelson configuration of FIG. 1 or the Mach-Zehnder configuration of FIG. 2 the total optical paths from source to detector include a double pass to the scattering center in the sample and back. Thus if the variation in apparent position D is five times the axial resolution, then the variation across the spectrum of the difference in group delay between the complete sample and reference paths is ten times the axial resolution. A variation in relative group delay of at least ten times the axial resolution is preferred to provide sufficient blurring of the unwanted image.

The degree of mismatch in chromatic dispersion determines the rate at which the relative optical group delay varies across the spectrum, so an OCT system that records spectra over a larger spectral range ΔQ will show a greater total variation in relative group delay for a given amount of dispersion mismatch. Alternatively, an OCT system that records spectra over a larger spectral range ΔQ requires less chromatic dispersion mismatch to produce the same total variation in relative group delay.

In images such as that shown in FIG. 5, the numerical correction of dispersion mismatch is performed independently for each column of these raster images. Therefore the dispersion correction can be tailored for each transverse location.

Figure 6:
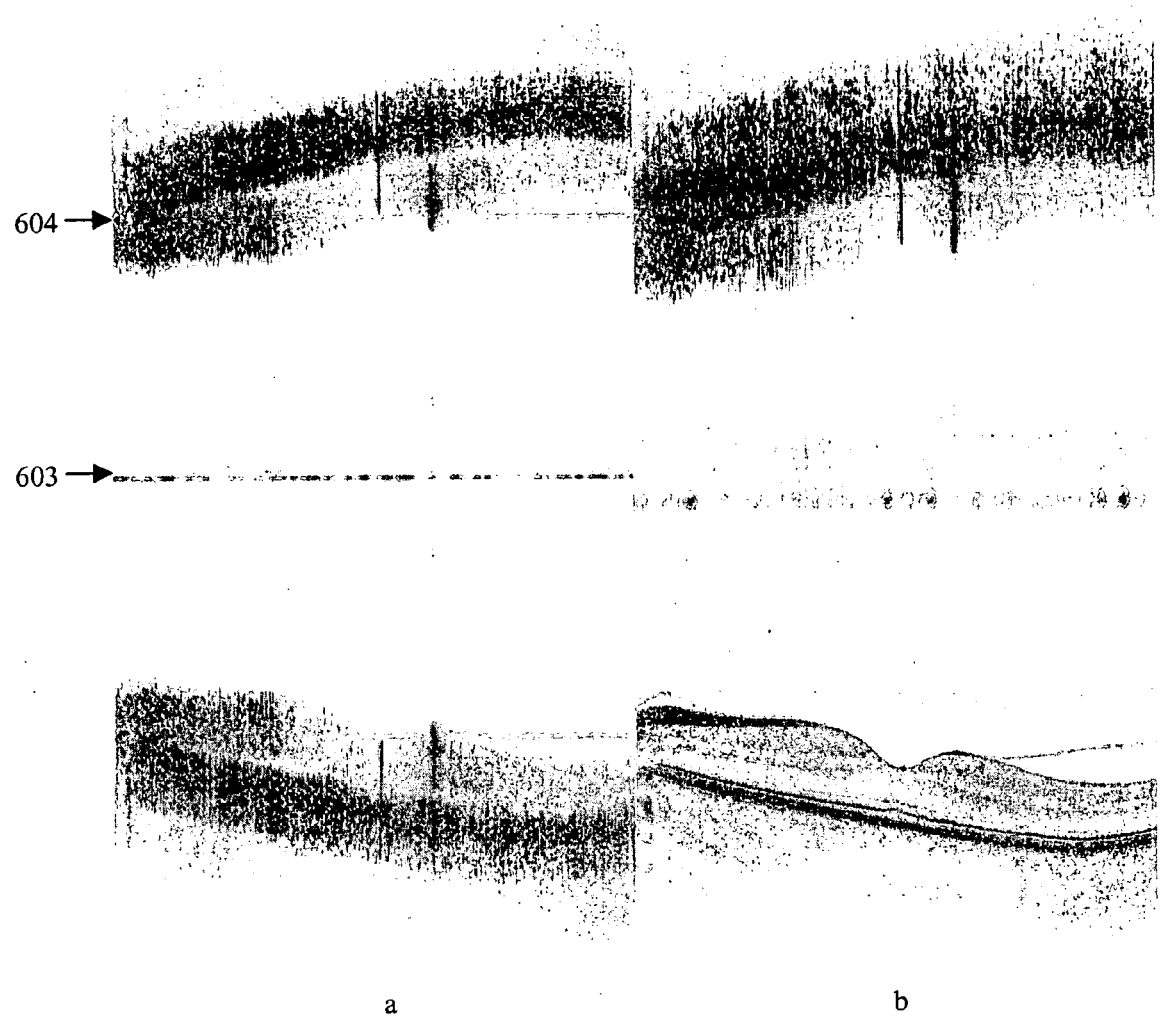
FIG. 6 shows OCT images of human eye tissue, with the undesired mirror images significantly blurred by the technique disclosed here.

FIG. 6a illustrates a situation in which the tissue has been moved down in the field of view, and in which the dispersion mismatch has not been corrected. The horizontal artifact 603 at the center of the image is the residual artifact 503 described above. The second horizontal artifact 604 comes from periodic noise in the detection electronics.

FIG. 6b illustrates the results of numerical compensation. The desired image is sharpened, while the mirror image is further blurred. The second horizontal artifact 604 is blurred and reduced in intensity.

Figure 7:
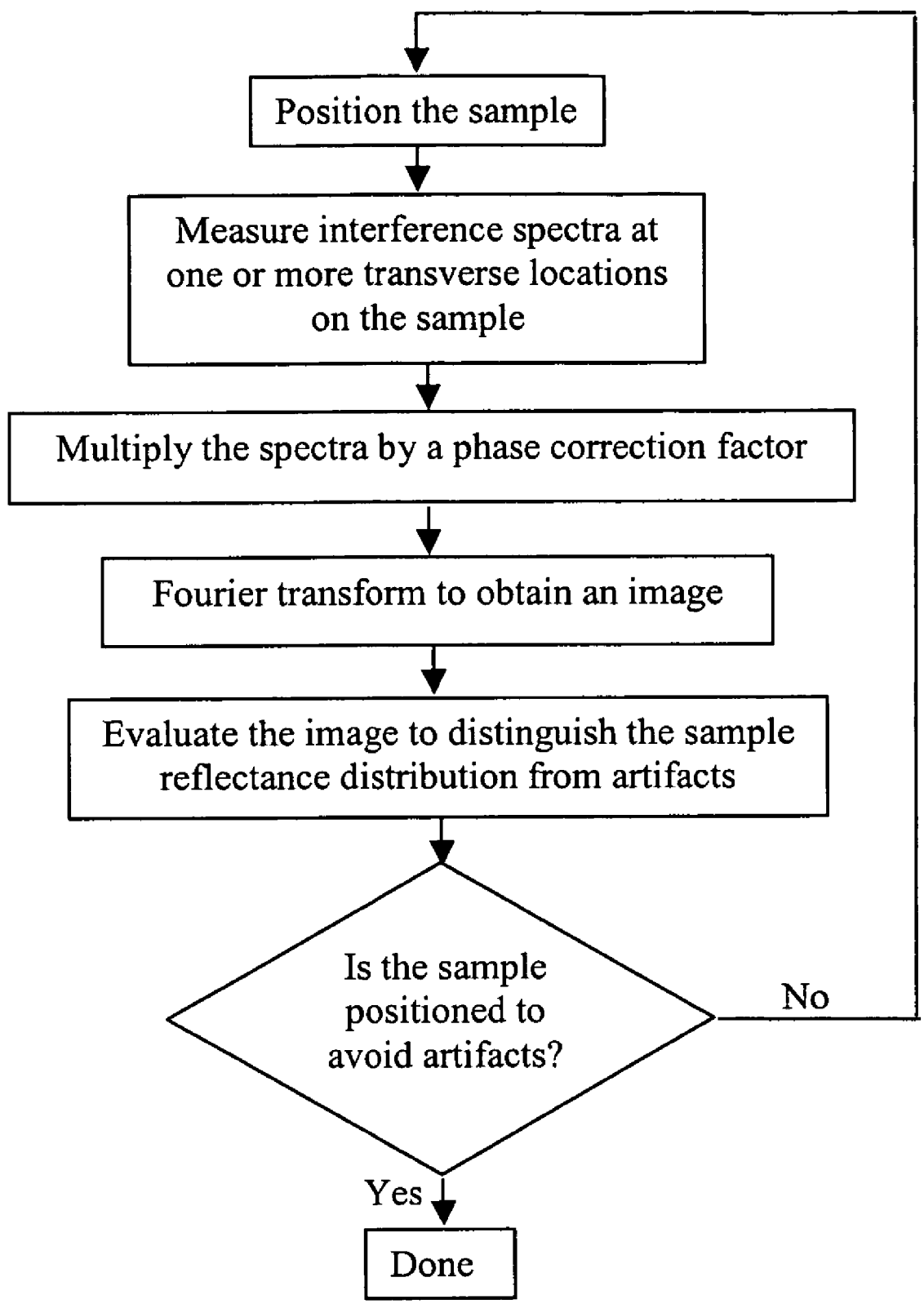
FIG. 7 illustrates a procedure for separating the desired OCT image from artifacts of Fourier-domain OCT.

FIG. 7 outlines a procedure for obtaining OCT images with suppressed artifacts, given an OCT instrument in which the chromatic dispersion mismatch is sufficient to allow the user to distinguish the desired image from the mirror image. One positions in the sample path a sample that may contain scattering structures over an unknown range of depths. One or more interference spectra are measured, possibly with the sample beam illuminating several transverse locations on the sample. The measured spectra are multiplied by the phase correction factor $e^{-i\phi_D}$. This factor cancels the effects of mismatched chromatic dispersion for the true image, but increases the blurring effects of mismatched chromatic dispersion for the mirror image artifact and pattern noise artifacts. The Fourier transform of the corrected spectra shows qualitative differences between the true image and artifacts of Fourier-domain OCT, allowing the operator to distinguish artifacts from the true image. The operator can optionally reposition the sample and repeat the OCT imaging procedure, so that the image of any region of interest in the sample is well-separated from artifacts.

Chromatic dispersion mismatch can also be used to compensate for non-uniform sampling of the interference spectra. In spectral-domain OCT the combined light is typically dispersed by a prism or diffraction grating and measured by a camera. The dispersion mechanism maps optical frequency onto position on the camera, but this mapping is in general non-linear and the samples of the interference spectrum P(q) are non-uniform in q. In swept-source OCT optical frequency varies as a function of time, and the mapping from optical frequency on to the time of measurement is in general non-linear. Interference spectra P(q) are conveniently sampled uniformly in time, which sampling will be non-uniform in q.

Typically the interference spectra are re-mapped from the coordinate along which they were measured onto a quantity linear in q. The resampling operation is computationally expensive, with operation count comparable to the Fourier transform. Resampling involves interpolation between measured data points, which can be performed using Fourier transform methods, or by interpolation kernels as described by Smith and Gossett. Wojtkowski et al. (*Optics Express* 12: 2404-2422) disclose a related technique in which the resampling step, normally used for correction of non-uniform sampling, is adjusted to compensate for residual dispersion mismatch. Instead, one can choose the mismatch between dispersion in the paths of the interferometer so that the variation in frequency of the fringes compensates for the non-uniformity of sampling. By way of example, a spectrometer in approximately Littrow configuration covering the frequency range from 750 nm to 850 nm will encode optical frequency q onto position x approximately as $x=q-0.15 \mu m\ q^2$. If such a spectrometer is used with an interferometer having a phase mismatch $\phi_D=360\ \mu m^2\ q^2$ due to chromatic dispersion, then the recorded fringes have the form $$\cos(2qz+\phi_D) \approx \cos[2xz+(360\ \mu m^2+0.30\ \mu m\ z)q^2].$$

At the position z=−1.2 mm, the spectrometer mapping cancels the effect of mismatched dispersion, giving fringes uniformly spaced as a function of x, so a direct Fourier transform of the data sampled in x will provide an image that is sharp near z=−1.2 mm. This method uses less processing to produce an image that is sharp over a limited range of depths. Specifically, the image remains sharp so long as the coefficient $(360\ \mu m^2+0.30\ \mu m\ z)$ is less than the square of the axial resolution of the OCT system, as explained by Fercher et al. (*Optics Communications* 204: 67-74). For a system with 10 μm resolution, the image remains sharp on this 10 μm scale over a range of depths z=−1.2 mm±0.3 mm. An analogous method is available in swept-source OCT, where the potentially nonlinear relation between instantaneous optical frequency of the source and time takes the place of the nonlinear mapping between optical frequency and position along the spectrum.

Figure 8:
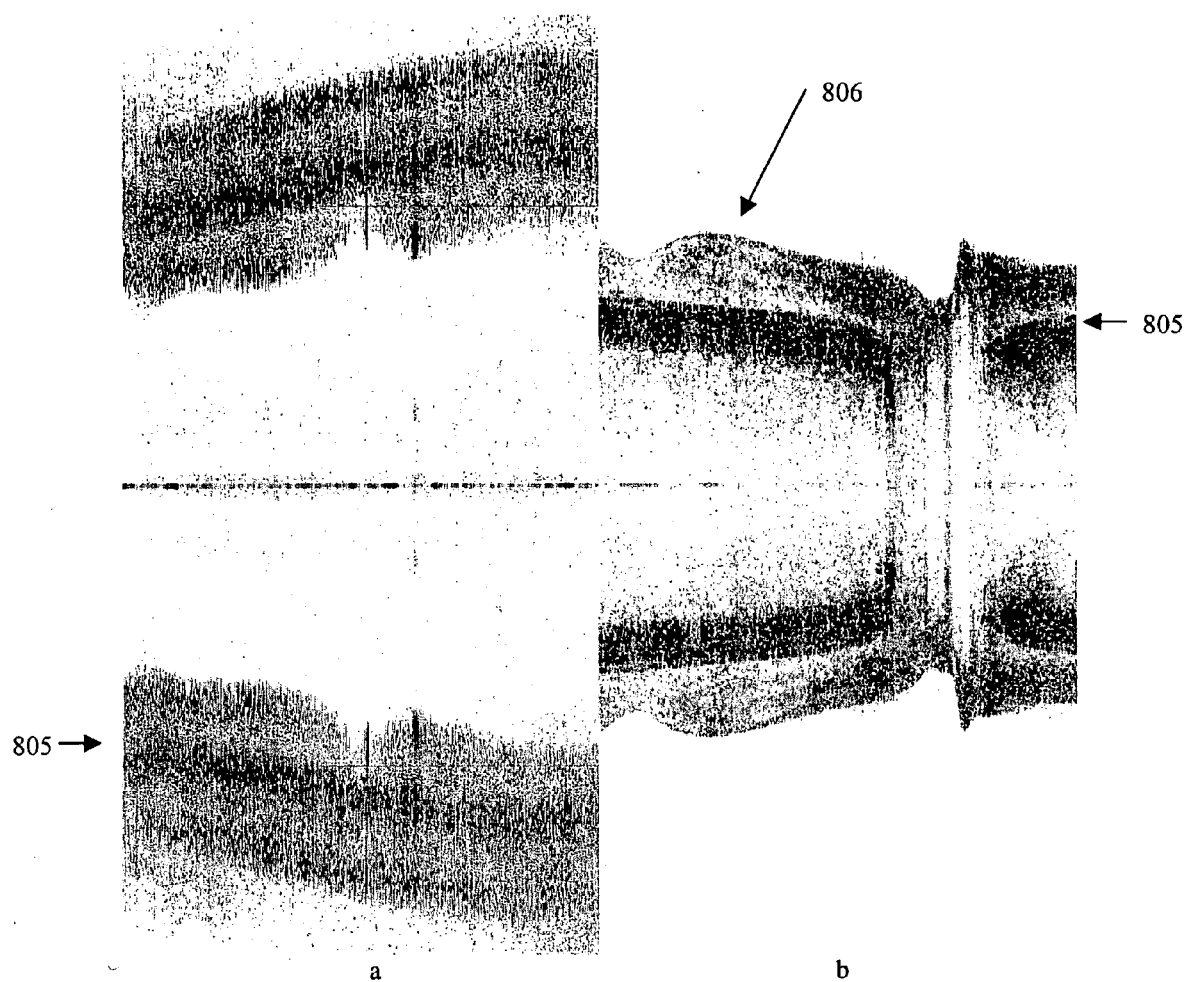
FIG. 8 shows OCT images of human eye tissue, for which chromatic dispersion mismatch was used to cancel the effect of nonlinear sampling of the OCT interference spectra.

FIG. 8 illustrates the results of using chromatic dispersion to compensate for non-uniform sampling of the interference spectrum. In this situation, the effects cancel for tissue near z=−1 mm, that is, for tissue approximately 1 mm closer to the interferometer than the z=0 position. This position appears above the center of the images in FIG. 8, higher than the z=0 line by approximately one quarter the image height.

In FIG. 8a, the sample 805 is too far from the interferometer, too low in the picture for the blurring effects of non-uniform sampling and chromatic dispersion to cancel. In FIG. 8b the same sample is placed closer to the interferometer (and has been moved slightly to the left). The image now appears approximately sharp, for a limited range of depths near the position of tissue membrane 806 within the sample. The images in FIGS. 8a and 8b are symmetric, because they are comprised of the intensities of the Fourier transforms of the real-valued function P(x). However, the condition for cancellation of the two blurring effects, non-uniform sampling and chromatic dispersion, depends on the physical position z of the sample and is sensitive to the sign of z. In this application it is preferred to display only the upper halves of the images in FIGS. 8a and 8b. The cancellation which results in a sharp image can be used to distinguish the desired image, in the upper half of FIG. 8b, from the inverted mirror image, in the upper half of FIG. 8a.

Another application of chromatic dispersion mismatch is in conjunction with phase shifting methods to remove the mirror image. Phase shifting methods to remove the mirror image are described, for example, by Leitgeb. et al. (*Optics Letters* 28: 2201-2203). As mentioned earlier, one difficulty of sequential phase shift methods is that motion of the sample causes an un-controlled phase shift between exposures. An exemplary method of phase shifting is to measure the same tissue with OCT twice, with the phase of the reference beam changed by nominally 90° between measurements. Apparatus to perform the phase shifting are described in co-pending U.S. patent application Ser. No. 10/933,795. We denote the two measurements of the interference spectra by $$A(q) = \int r(z)e^{i2qz}dz + \int r(z)e^{-i2qz-i2\phi_D}dz$$

$$B(q) = \beta \int r(z)e^{i2qz}dz + \beta^* \int r(-z)e^{i2qz-i2\phi_D}dz$$

where $\beta$ is the complex-valued ratio of the electric field in the reference beam for the first measured phase to the electric field for the second measured phase, and $\beta^*$ is its complex conjugate. Often the ratio $\beta$ has a phase that is proportional to optical frequency q ($\beta = \rho e^{-i2q\Delta}$ with constants $\rho$ and $\Delta$) because typical methods of producing the phase shifts by changing the length of the reference arm will cause a phase shift proportional to q, as will a displacements of the sample.

Given the two measurements A and B one forms the linear combination using the best available estimate b of the actual ratio $\beta$ $$C(q) = b^* A(q) - B(q)$$

$$= (b^* - \beta)\int r(z)e^{i2qz}dz + (b^* - \beta^*)\int r(-z)e^{i2qz-i2\phi_D}dz$$

in which the unwanted mirror image is suppressed to the extent that $b \approx \beta$. Errors as small as 1% in the estimation of $\beta$ are typically visible on conventional OCT images, because these images typically contain useful information spanning several orders of magnitude in signal intensity; a mirror image only 1% the amplitude of the true image will still be within the dynamic range typically presented, and visible in the logarithmic grayscale typically used for OCT image presentation. One particular cause of an error in b is motion of the sample between recording measurement A and recording measurement B.

Published work has attempted to estimate the true ratio $\beta$ by adjusting the parameter b so as to optimize the image reconstructed from combination C (for example, Cyganek et al., *Proceedings of SPIE* 5316:248). These methods require a metric to judge the correctness of the resulting image. When chromatic dispersion is matched, the mirror image produces a symmetric image, and image asymmetry has been used as a metric for the degree of removal of the mirror image. Highly asymmetric images are then judged more likely to be correct.

Figure 9:
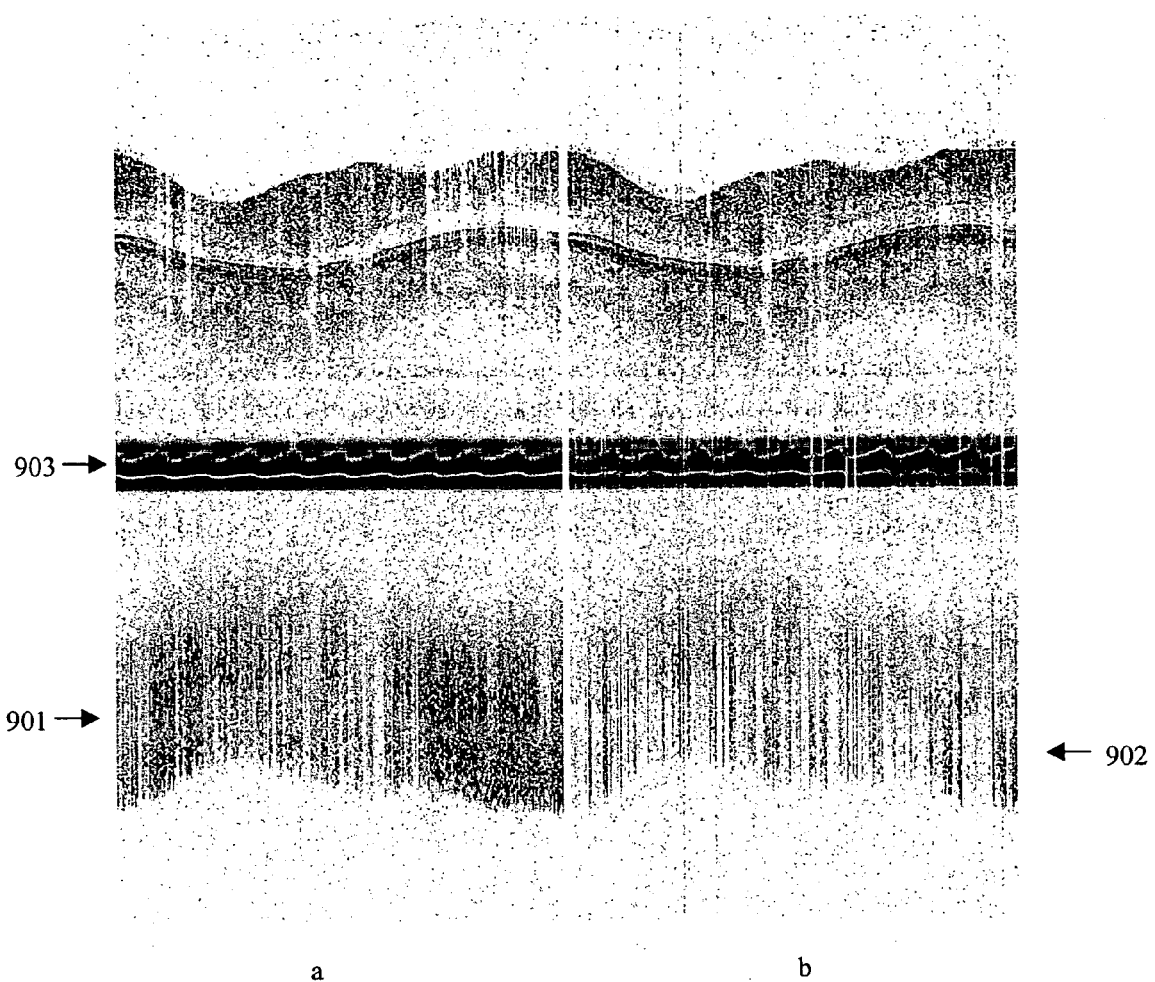
FIG. 9 shows OCT images of human eye tissue, reconstructed from phase-shifted measurements, illustrating an improvement available when the measurements are acquired with chromatic dispersion mismatch.

When the chromatic dispersion is significantly mismatched, the mirror image is blurred compared to the desired image, and thus the mirror image has lower contrast. Measures of image contrast can be used to judge the degree to which the mirror image has been removed. FIG. 9 shows reconstruction of an OCT image of a human eye acquired with reference phases alternating between 0° and 90°. The time between acquisition of the spectra was 200 microseconds. This type of sample can be expected to move approximately 0.1 microns longitudinally in this time interval; such movement is significant compared to the 0.8 micron wavelength of light used, and will create a significant phase shift in the sample reflectivity. For FIG. 9a the nominal phase shifts in the reference arm only were used to determine the coefficient b in image reconstruction. In this example we use the two phases of measurement to reduce the mirror image 901; we do not attempt to reduce the autocorrelation and low-frequency artifacts visible at indication 903 in these images, although these artifacts can be reduced by extensions of the phase shift technique (Leitgeb, R. A., et al. *Optics Letters* 28(22): 2201-2203). The mirror image 901 is suppressed only for those longitudinal scans near the center of the image, presumably those scans for which the sample happened to be relatively still. For FIG. 9b, the coefficient b was chosen individually for each longitudinal scattering profile to maximize image contrast in the corresponding column of the image. The mirror image 902 is significantly suppressed for most columns in the image.

The measure of contrast used to generate FIG. 9b was the mean-squared intensity of the each longitudinal scan, after the scan was normalized to have constant total intensity:

$$\int |r(z)|^4 dz / (\int |r(z)|^2 dz)^2,$$

where the reflectivity profile r(z) was determined from the linear combination C(q). Alternate measures of contrast can be used. Other operations made directly on the longitudinal scan can be used, such as the peak intensity or an entropy measure such as $\int |r(z)|^2 \log|r(z)| dz$. Alternatively, if the image is expressed as an array of pixels, statistics on the distribution of pixel intensities, such as the variance, skew, or kurtosis, can be used as measures of contrast.

Although various embodiments that incorporate the teachings of the present invention have been shown and described in detail herein, those skilled in the art can readily devise many other varied embodiments that still incorporate these teachings. For example, the difference in chromatic dispersion, effected by use of differing optical materials in the sample and reference paths in the preferred embodiment, can alternatively be achieved using any optical element that provides significant chromatic dispersion; the Gires-Tournois interferometer, and the pair of diffraction gratings, are two devices often used for this purpose (Siegman, A. E., *Lasers*, section 9.3).

The following references are hereby incorporated herein by reference.

US Patent Documents

U.S. Pat. No. 6,385,358 Everett et al. Birefringence insensitive optical coherence domain reflectometry system U.S. Pat. No. 6,615,072 Izatt et al. Optical Imaging Device U.S. Pat. No. 6,882,431 Teich et al. Quantum Optical Coherence Tomography U.S. Pat. No. 6,618,152 Toida Optical coherence tomography apparatus using optical-waveguide structure which reduces pulse width of low-coherence light U.S. Pat. No. 6,282,011 Tearney, et al. Grating based phase control optical delay line U.S. Pat. No. 5,321,501 Swanson, E., et al. "Method and apparatus for optical imaging with means for controlling the longitudinal range of the sample"

U.S. Pat. No. 5,956,355 Swanson, E., and S. R. Chinn, "Method and apparatus for performing optical measurements using a rapidly frequency-tuned laser"

U.S. patent application Ser. No. 10/933,795 Everett, M, et al., "A patterned spinning disk based optical phase shifter for spectral domain optical coherence tomography"

U.S. Patent Publication No. 2004/0239938 Izatt et al., "System for Fourier domain optical coherence tomography"

Other Publications

Choma, M. A., M. V. Sarunic, C. Yang, and J. A. Izatt (2003). "Sensitivity advantage of swept source and Fourier domain optical coherence tomography." *Optics Express* 11(18): 2183-2189.

Marta Cyganek, M., M. Wojtkowski, P. Targowski, and A. Kowalczyk (2004) "Numerical estimation of the total phase shift in Complex Spectral OCT in vivo imaging" *Coherence Domain Optical Methods and Optical Coherence Tomography in Biomedicine VIII*, Proceedings of SPIE 5316:248-251.

De-Boer, J. F., B. Cense, B. H. Park, M. C. Pierce. G. J. Tearney, and B. Bouma, (2003). "Improved signal-to-noise ratio in spectral-domain compared with time-domain optical coherence tomography." *Optics Letters* 28(21): 2067-2069.

Fercher A. F, C. K. Hitzenberger, M. Sticker, R. Zawadzki, B. Karamata, T. Lasser (2001). "Numerical dispersion compensation for Partial Coherence Interferometry and Optical Coherence Tomography." *Optics Express* 9: 610-615.

Fercher, A. F., C. K. Hitzenberger, M. Sticker, R. Zawadzki, B. Karamata, T. Lasser (2002). "Dispersion compensation for optical coherence tomography depth-scan signals by a numerical technique" *Optics Communications* 204: 67-74.

Hitzenberger, C. K., A. Baumgartner, W. Drexler, A. F. Fercher, (1999). "Dispersion Effects in Partial Coherence Interferometry", *Journal of Biomedical Optics* 4(1): 144-151.

Leitgeb, R. A., et al. (2003). "Performance of Fourier domain vs. time domain optical coherence tomography." *Optics Express* 11(8): 889-894.

Leitgeb, R. A., et al. (2003). "Phase-shifting algorithm to achieve high-speed long-depth-range probing by frequency-domain optical coherence tomography." *Optics Letters* 28(22): 2201-2203

Marks, D. L., A. L. Oldenburg, J. J. Reynolds, S. A. Boppart (2003). "Digital algorithm for dispersion correction in optical coherence tomography for homogeneous and stratified media" *Applied Optics* 42: 204-217.

Saleh, B. E. A, and M. C. Teich, (1991) *Fundamentals of Photonics*, John Wiley and Sons.

Siegman, A. E., *Lasers*, University Science Books, Sausalito Calif., 1986.

Smith, J. O., P. Gossett (1984) "A Flexible Sampling-Rate Conversion Method" Proceedings (2): 19.4.1-19.4.4, IEEE Conference on Acoustics, Speech, and Signal Processing, San Diego, March 1984.

Smith, L. M. and C. C. Dobson (1989). "Absolute displacement measurements using modulation of the spectrum of white light in a Michelson interferometer." *Applied Optics* 28(15): 3339-3342

Targowski, P., M. Wojtkowski, Z. Kowalczyk, T. Bajraszewski, M. Szkolmowski, I. Gorczyńska, (2004) "Complex spectral OCT in human eye imaging in vivo" *Optics Communications* 229:79-84.

Wojtkowski, M., T. Bajraszewski, P. Targowski, A. Kowalczyk (2003). "Real-time in vivo imaging by high-speed spectral optical coherence tomography." *Optics Letters* 28(19): 1745-1747.

Wojtkowski, M., V. Srinivasan, T. H. Ho, J. G. Fujimoto, A. Kowalczyk, J. S. Duker (2004). "Ultrahigh-resolution, high-speed, Fourier domain optical coherence tomography and methods for dispersion compensation" *Optics Express* 12: Page: 2404-2422.

Yun, S. H., G. J. Tearney, J. F. de Boer, B. E. Bouma, (2004) "Removing the depth-degeneracy in optical frequency domain imaging with frequency shifting" *Optics Express* 12:4822-4828.

We claim:

1. A method for suppressing artifacts in the image of frequency domain optical coherence tomography, comprising the steps of:

providing a sample path and a reference path that differ in their chromatic dispersion so as to create a variation in relative group delay as a function of optical frequency between the sample and reference paths, wherein the relative group delay variation across the range of optical frequencies recorded is greater than ten times the axial resolution of the optical coherence tomography system;

separating optical radiation from an optical radiation source among the sample path and the reference path;

measuring as a function of optical frequency the combined radiation returned from the sample and reference paths, the measurement producing an interference spectrum;

multiplying the measured interference spectrum by a complex phase factor to compensate for the mismatch in chromatic dispersion; and processing the compensated interference spectrum to obtain information on the reflectance distribution in the sample path.

2. A method as recited in claim 1, further including the step of positioning a sample to return both optical radiation with optical path length longer than the reference optical path length, and optical radiation with optical path length shorter than the reference optical path length.

3. A method as recited in claim 2, further including the step of repositioning the sample to separate the actual reflectance distribution corresponding to sample features from artifacts of the frequency domain optical coherence tomography measurement.

4. A method as recited in claim 1, further comprising the steps of:

inducing a sequence of different phase shifts in the radiation in at least one of the reference or sample paths;

repeating the measuring and multiplying steps for the different phase shifts; and processing the results to suppress artifacts in the image.

5. A method as recited in claim 4, wherein said processing step includes generating a linear combination of the measurements at the different induced phase shifts, said combination including coefficients selected to best estimate the actual phase shift occurring between the sample and reference paths.

6. A method as recited in claim 5, wherein the coefficients are selected to maximize image contrast between reflection distribution from the sample and the artifacts.

7. A method as recited in claim 1, wherein the difference in chromatic dispersion between the sample and the reference path is chosen such that a reflection site at a chosen depth in the sample path produces interference fringes across the interference spectrum that are non-uniformly spaced with respect to the measured optical frequencies.

8. A method as recited in claim 7, wherein measuring step is performed with detection electronics and the artifacts which are to be suppressed arise from noise in said detection electronics.

9. A method as recited in claim 8, wherein the detection electronics include a camera and the artifacts which are to be suppressed arise from noise produced by the camera.

10. A method for suppressing artifacts in the image of frequency domain optical coherence tomography, comprising the steps of:
providing a sample path and a reference path that differ in their chromatic dispersion so as to create a relative group delay variation as a function of optical frequency between the sample and reference paths;
separating optical radiation from an optical radiation source among the sample path and the reference path;
positioning a sample to return both optical radiation with optical path length longer than the reference optical path length, and optical radiation with optical path length shorter than the reference optical path length;
measuring as a function of optical frequency the combined radiation returned from the sample and reference paths, the measurement producing an interference spectrum;
processing the measured interference spectrum to compensate for the mismatch in chromatic dispersion and using the compensated interference spectrum to obtain information on the reflectance distribution in the sample path;
generating an image based on the information on the reflectance distribution to allow the actual reflectance distribution corresponding to sample features to be distinguished from artifacts of the frequency domain optical coherence tomography measurement; and
repositioning the sample to separate the image of the actual sample features from the artifacts of the frequency domain optical coherence tomography measurement.

11. The method of claim 10, wherein the measuring and processing steps are repeated at several transversely separated locations on the sample to generate data which can be used to form a cross-sectional image of the sample.

12. The method of claim 10, wherein the relative group delay variation across the range of optical frequencies recorded is greater than ten times the axial resolution of the optical coherence tomography system.

13. The method of claim 10, wherein the difference in chromatic dispersion in the paths is created by use of different optical materials in the sample and reference paths.

14. The method of claim 10, wherein the difference in chromatic dispersion in the paths is created by use of one or more dispersive optical elements in the sample or reference paths.

15. The method of claim 10, wherein the interference spectrum is measured with an optical spectrometer.

16. The method of claim 10, wherein the interference spectrum is measured by varying the optical frequency of the optical radiation source.

17. The method of claim 10, wherein the optical coherence tomography is performed with a portion of a human eye as the sample.

18. The method of claim 10, wherein the optical coherence tomography is performed with the sample path routed through an endoscope, and wherein an interior part of the human body is the sample.

19. The method of claim 10, wherein the optical coherence tomography is performed with a section of human skin as the sample.

20. A method as recited in claim 10, wherein said processing step includes multiplying the measured interference spectrum by a complex phase factor to compensate for the mismatch in chromatic dispersion.

21. A method for suppressing artifacts in frequency domain optical coherence tomography comprising the steps of:
providing a sample path and a reference path that differ in their chromatic dispersion so as to create a relative group delay variation as a function of optical frequency between the sample and reference paths;
separating optical radiation from an optical radiation source among the sample path and the reference path;
measuring at a sequence of discrete optical frequencies the combined radiation returned from the sample and reference paths, the measurements producing an interference spectrum, wherein the measurements are taken with non-uniform spacing in optical frequency; and
processing the resulting interference spectrum to obtain information on the reflectance distribution in the sample path wherein the difference in chromatic dispersion is chosen such that a reflection site at a chosen depth in the sample path produces interference fringes that are uniformly spaced in the sequence of discrete optical frequencies used for the measurements.

* * * * *